(12) United States Patent
Mather et al.

(10) Patent No.: US 8,394,393 B2
(45) Date of Patent: Mar. 12, 2013

(54) SYSTEM AND METHOD FOR THE RELEASE OF NITRIC OXIDE USING NANOSCALE MEDIA

(75) Inventors: Patrick Mather, Manlius, NY (US); Ifeanyi Onyejewke, Syracuse, NY (US); Kazuki Ishida, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 13/081,059

(22) Filed: Apr. 6, 2011

(65) Prior Publication Data

US 2011/0244001 A1    Oct. 6, 2011

Related U.S. Application Data

(60) Provisional application No. 61/321,167, filed on Apr. 6, 2010.

(51) Int. Cl.
| | |
|---|---|
| *A61K 31/785* | (2006.01) |
| *A61K 9/00* | (2006.01) |
| *A61P 7/02* | (2006.01) |
| *B29C 47/00* | (2006.01) |

(52) U.S. Cl. ............... 424/400; 264/465; 424/78.17; 424/78.35; 424/78.37; 424/78.38; 977/778; 977/788; 977/906

(58) Field of Classification Search ............ None
See application file for complete search history.

(56) References Cited

U.S. PATENT DOCUMENTS

| | | |
|---|---|---|
| 6,753,454 B1 | 6/2004 | Smith et al. |
| 2004/0131753 A1 | 7/2004 | Smith et al. |
| 2008/0286321 A1 | 11/2008 | Reneker et al. |
| 2009/0136410 A1 | 5/2009 | Smith |
| 2009/0148482 A1 | 6/2009 | Peters |

*Primary Examiner* — Suzanne Ziska
(74) *Attorney, Agent, or Firm* — David L. Nocilly; Bond Schoeneck & King

(57) ABSTRACT

A composite material containing polymeric nanofibers, themselves containing NO-donor molecules, imbibed with an elastomer matrix is permeable to both water and gas so that dissociation reactions in the presence of water releases NO gas in a sustained manner. The NO-donor nanofibers may be formed by synthesizing acceptable NO-donor molecules, blending such molecules in solution with PVP, PCL or PVAc, electrospinning the blend at relatively high voltage for form fiber mats, applying PDMS rubber to the fiber mat and crosslinking it. The resulting NO-releasing electrospun fiber composite may be used in medical devices such as catheters, stents, or vascular grafts, with the purpose of releasing nitric oxide within a controlled rate and for a sustained period of time, as well as other known medical applications for NO.

14 Claims, 14 Drawing Sheets

| Cycle | $\varepsilon_u$ (%) | $\varepsilon_m$ (%) | $\varepsilon_p$ (%) | $\varepsilon_p$ (N-1)(%) | $R_f$ (%) | $R_r$ (%) |
|---|---|---|---|---|---|---|
| 1 | 98.1 | 109.5 | 19.25 | 6.5 | 89.6 | 76.5 |
| 2 | 96.7 | 107.1 | 19.25 | 19.6 | 90.2 | 88.2 |
| 3 | 96.4 | 106.8 | 20.1 | 19.6 | 90.2 | 87.5 |

Figure 9(c)

SYSTEM AND METHOD FOR THE RELEASE OF NITRIC OXIDE USING NANOSCALE MEDIA

CROSS-REFERENCE TO RELATED APPLICATIONS

The present application claims priority to U.S. Provisional Application No. 61/321,167, filed on Apr. 6, 2010.

BACKGROUND OF THE INVENTION

1. Field of the Invention

The present invention relates to systems and method for releasing nitric oxide and, more particularly, toward elastomeric fibers for the release of nitric oxide.

2. Description of the Related Art

Thrombosis is a common phenomena associated with the use of many blood-contacting medical devices. This adverse affect often occurs due to the fact that a number of these devices are fabricated from hydrophobic materials that enable the absorption of proteins on the surfaces of the device, consequently leading to activation of coagulation factors. A plethora of molecular approaches (additives) have been implemented to try to mitigate this occurrence, including Plavix™, coumadin, and heparin. However, the effectiveness of these treatments is limited and often results in adverse effects, such as hemorrhaging in other parts of the body. Consequently, there has been growing interest in the application of nitric oxide (NO) for the prevention of platelet aggregation within the last two decades.

Nitric oxide is a simple diatomic molecule involved in a number of bioregulatory functions ranging from vasodilatation and endothelial cell proliferation to the prevention of platelet aggregation. One aspect of our NO studies has focused on the anticoagulation properties of nitric oxide and the potential application of this NO-releasing compound as thrombo-resistant coatings on blood-contacting medical devices. Herein, we will present our invention, which offers NO-modified compounds, within a nanofiber composite structure capable of sustained release of nitric oxide at physiological conditions.

Nitric oxide has a number of other functions beyond those mentioned above. For example, NO possesses antibacterial properties against both gram-positive and gram-negative bacteria. Thus, our present invention is anticipated to possess additional useful properties beyond prevention of thrombus formation. The NO-modified compounds could also serve as antimicrobial coatings that prevent biofilm infections, an undesirable phenomenon that is considered a common threat to hospitalized patients afflicted with exposed wounds.

BRIEF SUMMARY OF THE INVENTION

The present invention comprises a nanofiber containing NO-donor molecules that is infiltrated with an elastomeric composite. More particularly, the present invention involves three components: (i) a nanofiber; (ii) an NO donor attached to the nanofibers; and (iii) an elastomeric matrix infiltrated into the nanofiber/NO donors. The NO-releasing electrospun fibers have a diameter in the nanometer range and the drug release rate is regulated by the elastomeric polymer matrix, which encapsulates the fibers, forming a two-part composite. Specifically, a prepared nanofiber mat containing NO-donor molecules is infiltrated with an elastomeric matrix that has desirable permeability to both water and gas molecules.

The present invention has permeability to both water and gas and, upon contact of the present invention with water or blood, water will permeate through the elastomeric matrix to the NO donor molecules, thereby resulting in a dissociation reaction that releases NO gas that will, in turn, permeate through the elastomeric barrier. The NO-donor nanofibers of the present invention may be formed by synthesizing acceptable NO-donors by NO loading the polymers in solution. After the polymers have been NO-modified, the solution is blended with PVP, PCL or PVAc and electrospun at relatively high voltage to form a fiber mat. PDMS is then applied to the fiber mat and allowed to cure. The resulting NO-releasing electrospun fibers may be used in medical devices such as catheters, stents, or vascular grafts, with the purpose of releasing nitric oxide within a controlled rate and for a sustained period of time, as well as other know medical applications for NO.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 6A:
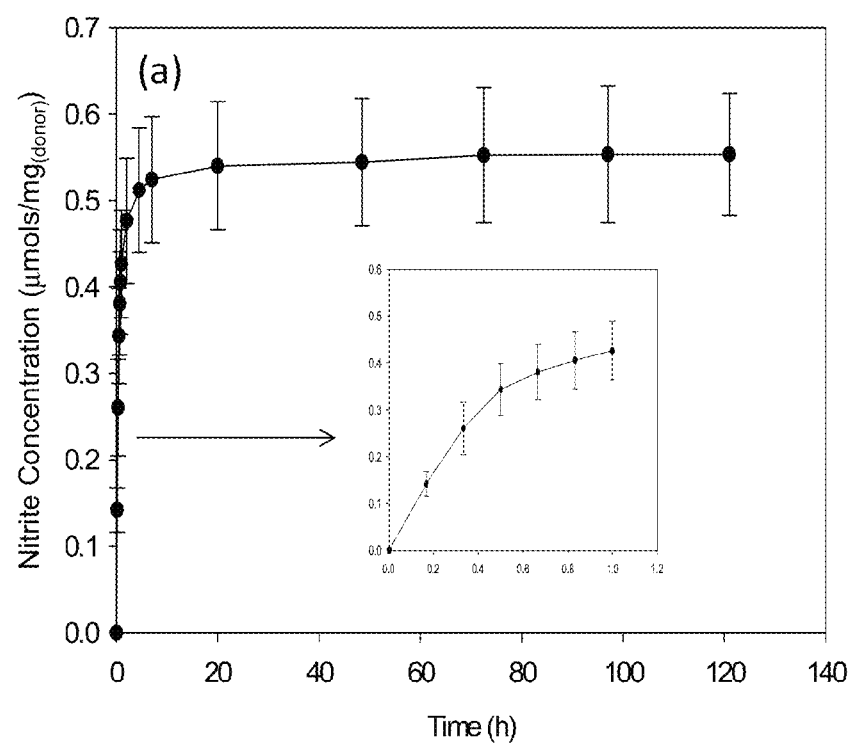
Figure 6B:
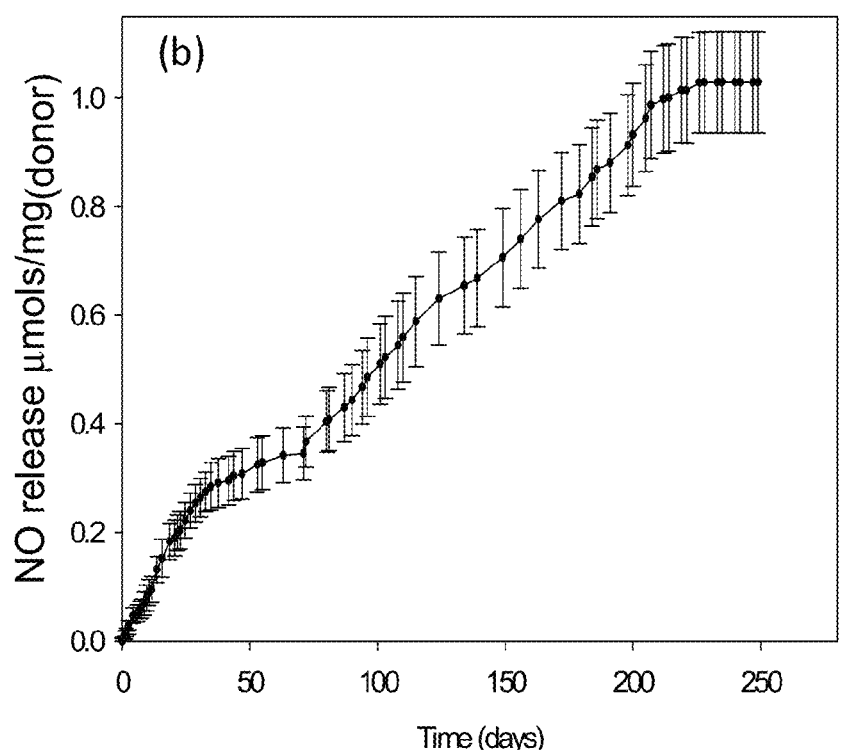

FIGS. 5($a$) and ($b$) are charts comparing NO release from OctaAPOSS/PCL fiber mats both with, FIG. 5($a$), and without, FIG. 5($b$), integration of a crosslinked PDMS (Sylgard™ 184) matrix;

FIGS. 6($a$) and ($b$) are charts comparing (a) NO release from PVAc-DETA/NO fibers (with no elastomer) and (b) the NO-release curve from $PDMS\_PVAc_{98.5}$-$DETA/NO_{1.5}$ composite showing a slight plateau at day 72, then increase release for 220 days.

Figure 7A:
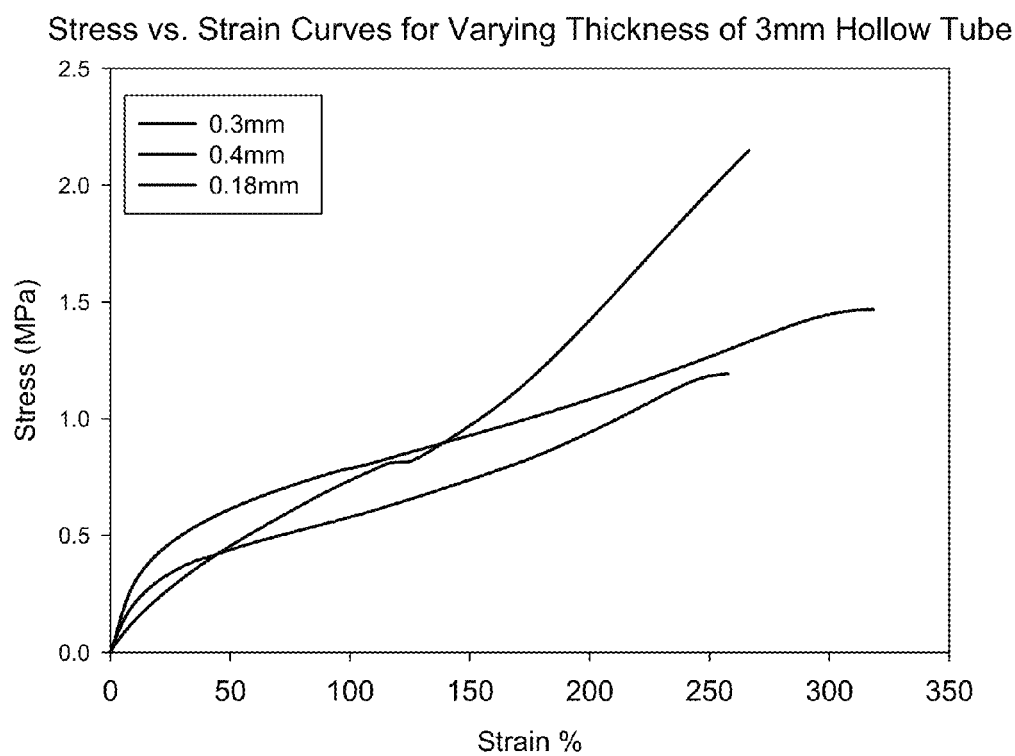
Figure 7B:
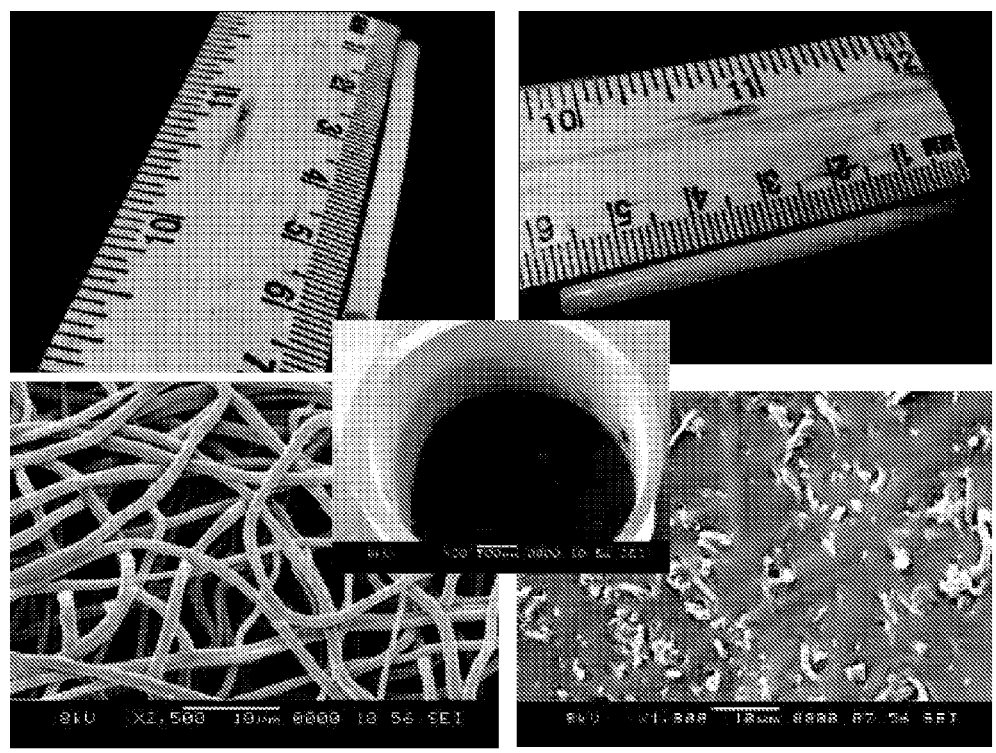
Figure 8:
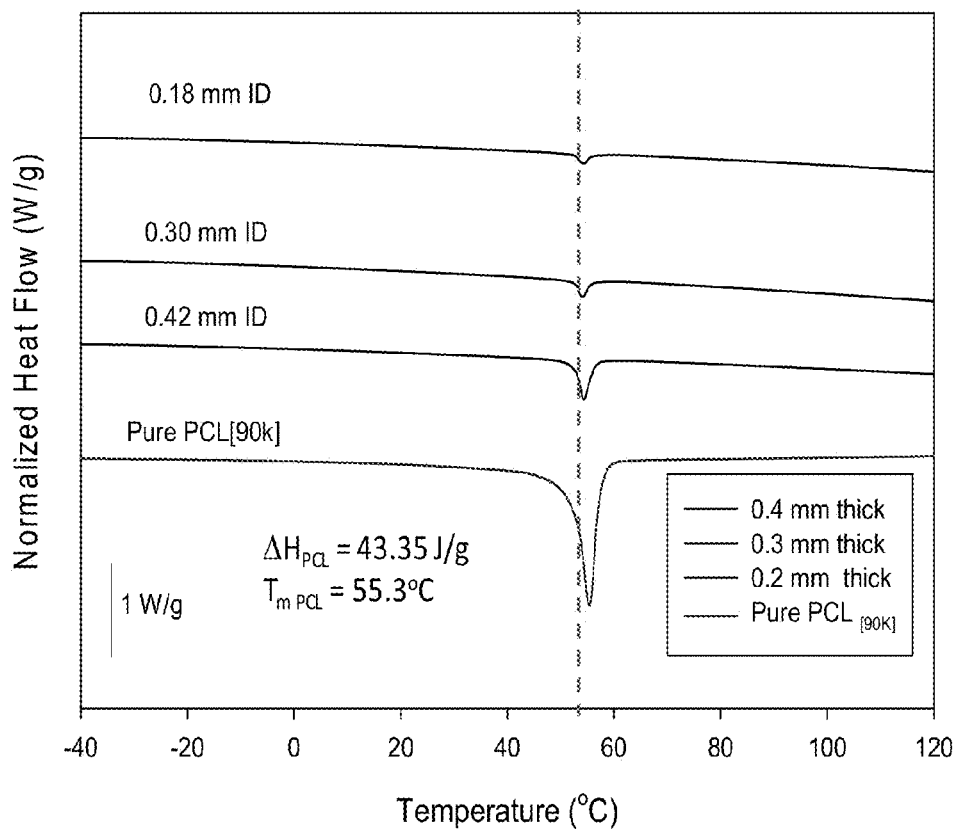
Figure 9A:
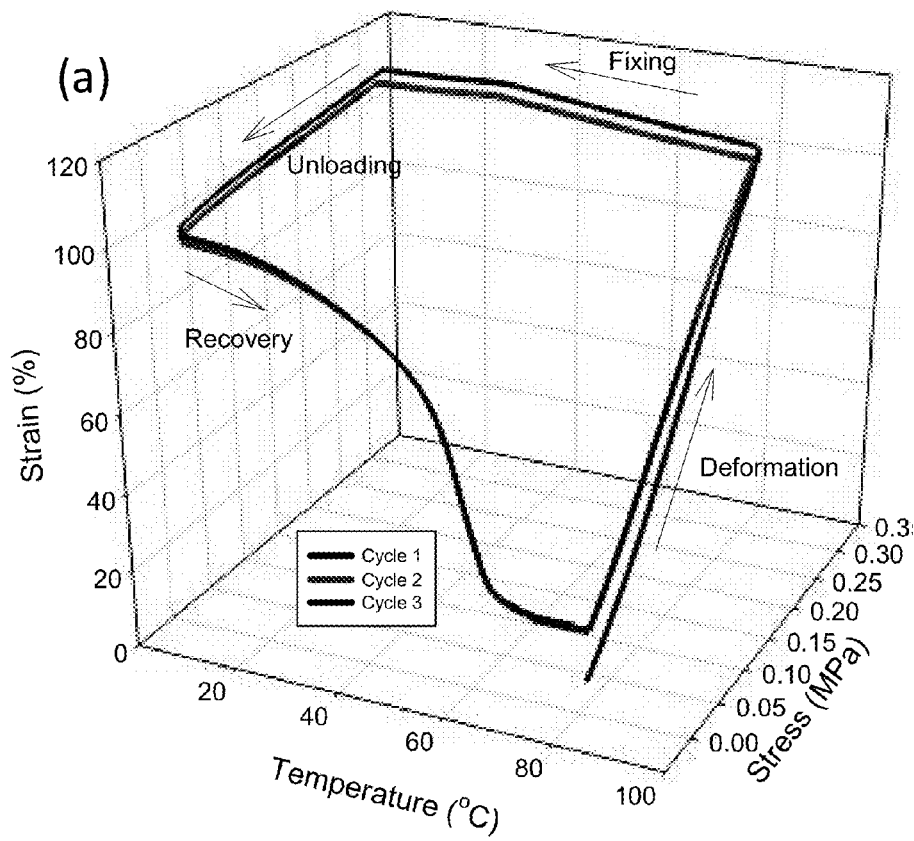
Figure 9B:
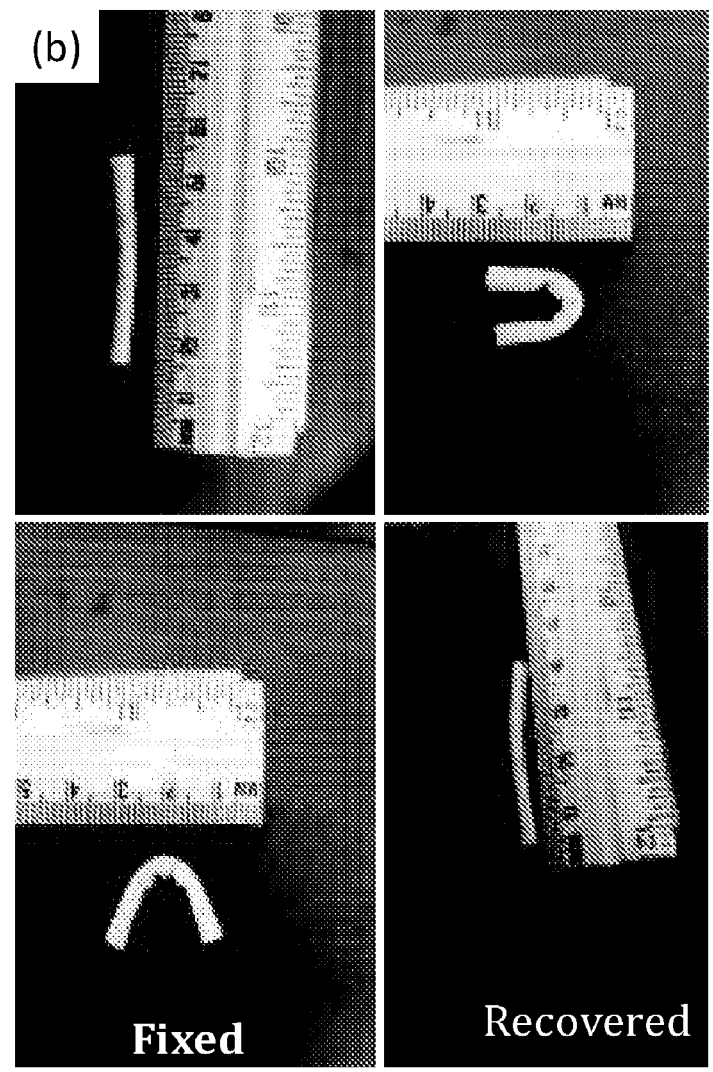

FIGS. 7($a$) is a chart of the stress vs. strain curve of PCL conduit with varying thickness and FIG. 7($b$) are a series of images of PCL(90 k) hollow tube fibers conduit capable of holding NO donors for sustained NO delivery;

FIG. 8 is a graph of DSC $2^{nd}$ heating traces showing melting endotherms for neat PCL and PCL/Sylgard composites with varying thickness. The data shows increase in tube thickness is associated with increase in PCL fiber density which is quantifiable by $\Delta H$; and FIG. 9 is a demonstration of 1-way-shape-memory properties of Sylgard/PCL as previously reported by the inventors, where FIG. 9($a$) is a stress-temperature-strain plot showing one-way shape cycle of the composite, FIG. 9($b$) is a series of images showing utilization of heat induced shape-memory to fix and recover hollow tube conduit for vascular graft application, and FIG. 9($c$) is a table showing fixing and recovery percentage with $\epsilon_u$, $\epsilon_m$, $\epsilon_p$ and N representing strain of the material before unloading and after unloading (100% indicates complete fixing or recovery).

DETAILED DESCRIPTION OF THE INVENTION

Figure 1:
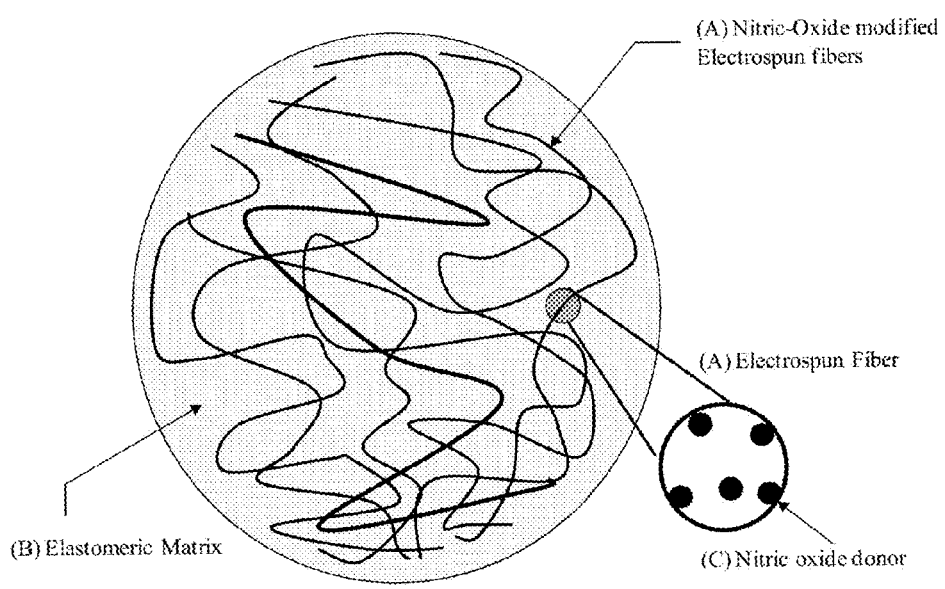
FIG. 1 is a schematic of a NO-releasing composite material according to the present invention.

Referring now to the drawings, wherein like reference numerals refer to like parts throughout, the present invention involves nitric oxide (NO) releasing electrospun fibers whose diameter is in the nanometer range and whose release rate is regulated by an elastomeric polymer matrix binding the fibers together. In particular, a prepared nanofiber containing NO-donor molecules is infiltrated with an elastomeric composite that has desirable permeability to both water and gas, as seen in FIG. 1. Upon contact of this structure with water or blood, water will permeate through the elastomeric matrix to the NO donor molecules (e.g., diazeniumdiolated OctaAPOSS), following which a dissociation reaction will occur, releasing NO gas. This gas will, in turn, permeate through the same elastomeric barrier before release into the PBS or blood environment. The rate limiting steps appear to be the water permeation and the NO gas permeation, the former being the slowest. Without the presence of an elastomer, a spontaneous release of nitric oxide from the fibers would occur within a relatively shorter duration of time. Preliminary data (examples) substantiates this expectation.

Figure 2:
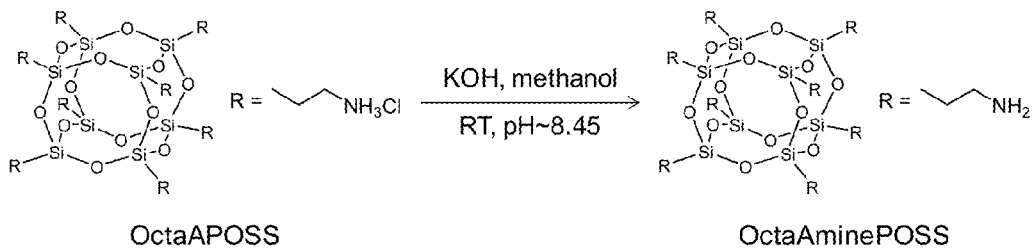
FIG. 2 is a schematic of OctaAPOSS modified with sixteen moles of NO per molecule according to the present invention.
Figure 2:
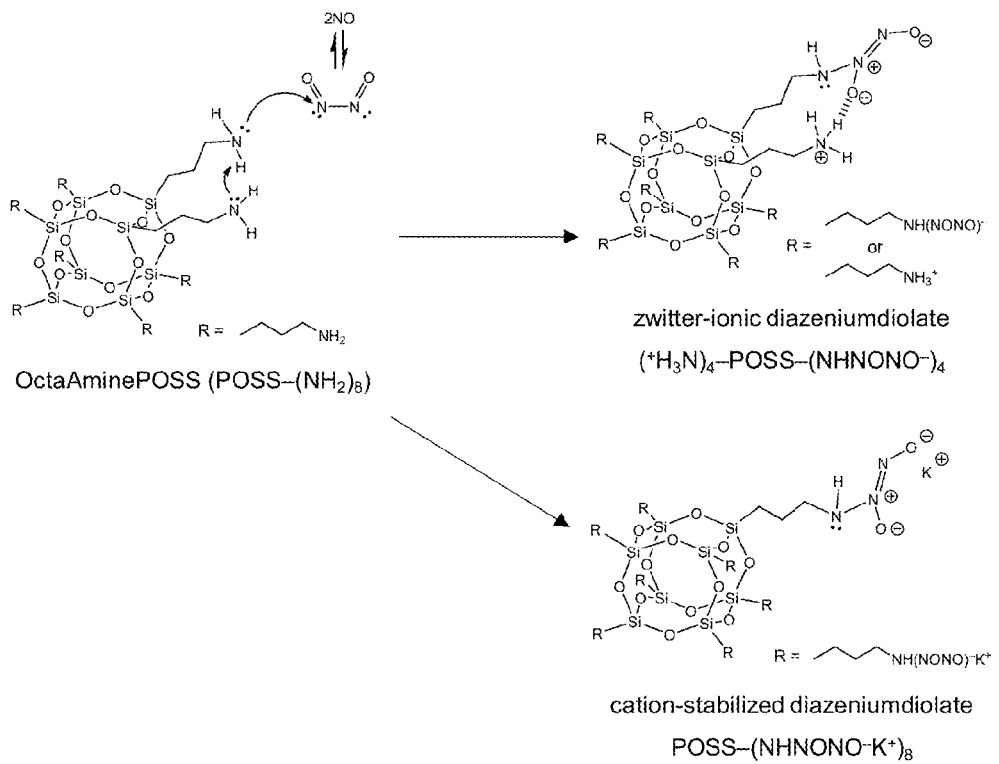
Figure 3:
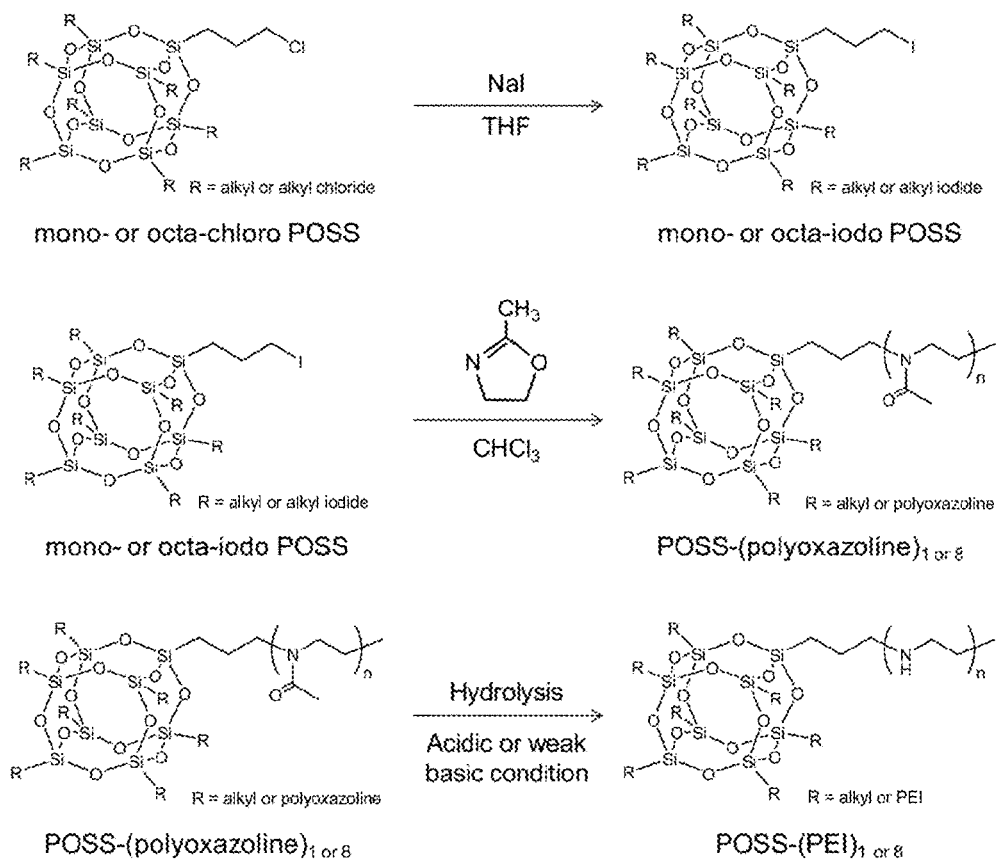
FIG. 3 is a schematic of the synthesis of PEI-POSS according to the present invention.

The present invention utilizes a group of nitric oxide-modified materials known as NO-Donors. Nitric oxide donors are molecules that are capable of releasing NO spontaneously through various mechanisms including thermal and photochemical decomposition. NO donors are often classified into two main groups: Diazeniumdiolates and S-Nitrosothiols. The present invention utilizes the diazeniumdiolation group of molecules because such NO compounds are formed by the facile reaction between the primary or secondary amines present within the donor compounds and pressurized nitric oxide gas. The resulting molecule is a stable structure containing two-moles of nitric oxide per amine capable of dissociation upon contact with water. The main NO donor molecules used for the present invention have included linear poly(ethyleneimine) (LPEI), poly(vinylpyrrolidone) (PVP), poly(caprolactone) (PCL), OctaAmmonium POSS (OctaAPOSS), and PEI-POSS hybrid polymer. This choice of compounds was based mainly on their biocompatibility, electrospinnability, and past experience with the materials. OctaAPOSS, LPEI and PEI-POSS were selected based on the presence of nucleophilic primary or secondary amines, which would provide potential binding-sites for nitric oxide. OctaAPOSS has eight ammonium chloride ($-NH_3^+Cl^-$) alkyl arms that can be easily functionalized and modified to primary amines ($-NH_2$) under basic conditions, and is sequentially modified with nitric oxide. This NO-modified OctaAPOSS could potentially provide 8-fold the amount of nitric oxide produced by most NO-donors, as shown schematically in FIG. 2. The synthesis scheme for the preparation of PEI-POSS is shown in FIG. 3.

The primary challenge in the art associated with NO-releasing media is the ability to control the release rate of the gas from the compound. In order to obtain a more controlled release rate, the nanofiber mats of the present invention, fabricated from the compounds aforementioned, are imbibed with an elastomer, such as crosslinked polydimethylsiloxane (PDMS). The present invention may thus employ commercially available PDMS, Sylgard® 184, and silanol terminated PDMS have been utilized. Elastomers based on PDMS are permeable to gas and water molecules, owing primarily to the very low glass transition temperature ($T_g$). Such permeability is important to the present NO-releasing system, taking into consideration that NO donors release NO (gas permeation out) upon contact with water (water permeation in). Utilization of elastomers like PDMS in this manner will allow a more sustained release of NO from the fibers and would help to reduce the initial spontaneous "dump" of the gas once placed in aqueous solution (See FIG. 5(*b*), below, for the non-PDMS example). The benefits of regulating permeation via imbibition with PDMS (or other elastomers—such as biodegradable polyanhydride) in the form shown is two-fold: (i) maintaining nitric oxide concentration within a sub-toxic limit, and (ii) sustained release of NO spanning a range of time useful for healthcare. Such properties in a synthetic material render it biomimetic, behaving in a manner similar to endothelial cells, which are responsible for the synthesis and release of NO in human vasculature.

Diazeniumdiolation is the method used to synthesize diazeniumdiolates. The method is relatively simple, whereby materials are reacted with nitric oxide at relatively high pressure (ca. 70 psi) under vacuum and at room temperature for approximately 3 days. The main compounds utilized for these studies were placed in solution, contained in high-pressure glassware, and reacted with NO for approximately 3 days, though the time required for completion is likely much shorter.

Figure 4:
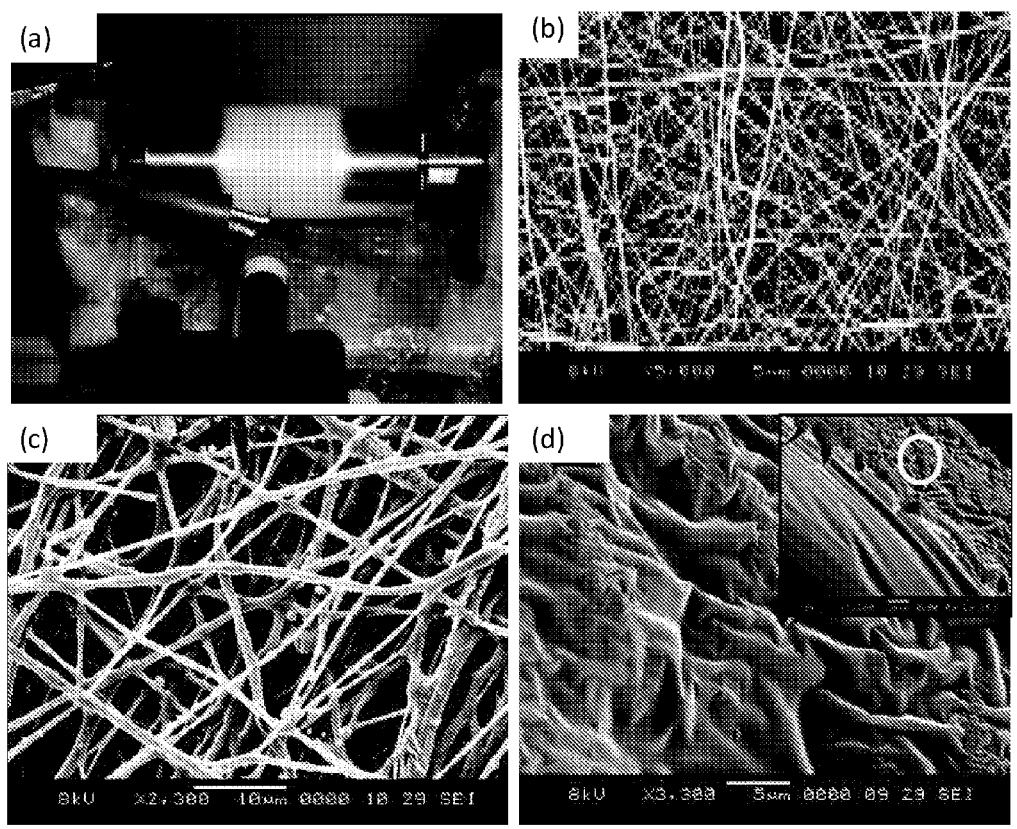
FIG. 4 are micrographs of: (a) the formation of e-spun fibers on collector; (b) e-spun 15 wt-% LPEI/PVP w/o NO, (c) 2 wt-% OctaAPOSS/KOH/PCL(90 k) w/NO; and (d) PDMS 2-wt % OctaAPOSS/KOH/PCL w/NO, according to the present invention.

The present invention utilizes electro-spinning techniques to produce non-woven fibrous mats. These e-spun fibers provide a high surface to volume ratio, which enhances mass transfer properties and improves homogeneity. For this invention, solutions of NO-modified OctaAPOSS, LPEI, PVAc, and PEI-POSS were e-spun to obtain uniform fiber mats containing NO donors. Some solutions were blended with PVP (Mw=360 k), PCL (Mw=90 k) or PVAc (Mw=260 k) prior to electrospinning in order to enhance fiber formation and spinnability of the solution. E-spun webs containing fibers with average diameter in the 100 nm-500 nm range were obtained. The process and example electron micrographs are shown in FIG. 4(*a*), (*b*), (*c*), (*d*). Previous work of the inventors revealed how to combine electrospun polymeric fibers with PDMS elastomer (e.g. Sylgard 184) to form an elastomeric composite material with shape memory properties.

While electrospinning is a technique that has been utilized and the combination of diazeniumdiolation of NO donors and electrospinning techniques exist, the present invention comprises two important and new elements to the formation of NO releasing media: (i) the use of OctaAmmoniumPOSS as the high loading-capacity and stable nitric oxide donor; and (ii) NO release rate regulation through the integration of an elastomeric within the fibers. The compounds used for the present invention and the affordance of spinnability adds to the uniqueness of the present invention.

The nitric oxide modification process for solutions containing LPEI was obtained from literature; however, for OctaAmmoniumPOSS the compound could not be NO-modified unless the reaction was conducted in a basic (pH>10) environment. In conventional work, sodium methoxide (NaOMe) was the basic salt used to create this basic environment. In the present invention, potassium hydroxide (KOH) was used. The pH of the solution needs to be between 10 and 12 for the reaction to occur without degradation of the POSS cage.

EXAMPLES

The synthesis of the NO-modified PDMS system of the present invention is a three-step process, as shown in FIG. 4. The first step is to NO-load the compound in solution (in most cases we have used methanol, ethanol or acetonitrile). The reaction is conducted at 70 psi with a reaction time of about 3 days. After the solution has been NO-modified, the second step is to blend it with PVP or PCL and electrospin the solution at relatively high voltage of approximately 15 kV. The third step is to apply PDMS to the fiber mat and allow $\geq 7$ days for curing. After the system has cured a release analysis in PBS may be conducted. The Griess Assay was used to determine the presence of nitrite in the PBS solution. The advantage of the NO releasing system of the present invention is that it provides a large surface to volume ratio and high NO loading capabilities, as well as a highly controlled releasing system.

Figure 5A:
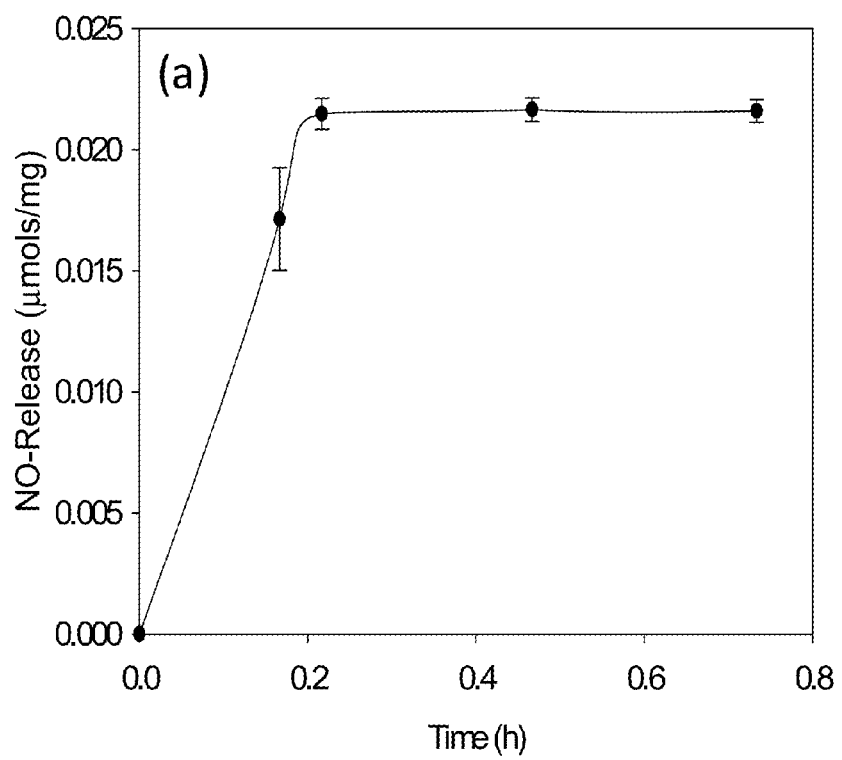
Figure 5B:
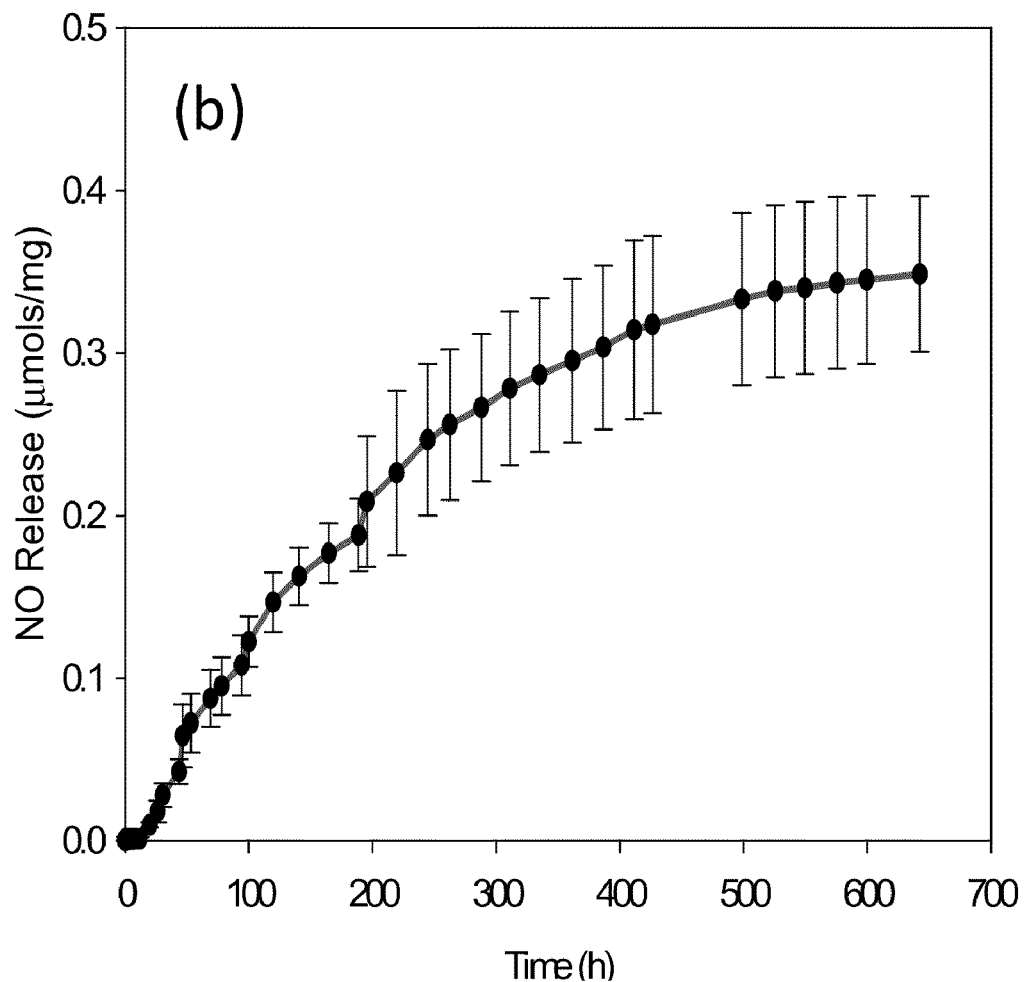

In FIG. 5(a), the plot shows NO release from the OctaAPOSS/PCL fibers without PDMS, as anticipated, a spontaneous release occurred within the first 20 min and plateaus out for most of the remaining 90 min. However, once PDMS is applied to the fibers the spontaneous release is significantly dampened and the release lasts for 27 days as opposed to 110 min as seen in FIG. 5b. The same test was conducted using another NO-donor-DETA/NO, entrapped in PVAc fibers. NO release study showed that the PVAc-DETA/NO fibers (without Sylgard) released 0.54±0.07 μmols/mg of NO for approximately 72.5 h. The release curve, FIG. 5(a), showed fairly large spontaneous release of NO within the first 1.5 h. However, FIG. 5(b) showed the elastomeric composite released 1.03±0.09 μmols/mg for over 220 days—almost double the concentration of NO released from the fibers without Sylgard. The NO release curve for the elastomeric composite appeared to have zero-order release for the first 30 days, following a slight declination or plateau and another increase in the release. The fortuitous increase around day 72 was not anticipated, however, this could have occurred due to the leaching of PDMS from the composite over time thus, exposing more DETA/NO initially entrapped within the fibers to water.

The ability of the present invention to use a variety of polymers and NO-donors, helped to successfully validate the generality of controlled and sustained NO release from the elastomeric nanocomposite system (see FIG. 6(a) and (b)). The results confirmed that the incorporation of DETA/NO into an elastomeric nanocomposite system attenuated the uncontrolled and spontaneous release of NO under physiological conditions, showing increase in the duration of NO release. There are a number of variables within the system that can be tailored or controlled, thus leaving a lot of room for further studies and characterization. However, NO release from the elastomeric composite for 220 days is very unique and advantageous. For this reason, the present NO-releasing elastomeric nanocomposite system could serve as an ideal candidate for the improvement of various localized biomaterials applications, including thromboresistant coatings, vascular grafts and wound healing applications.

Fabrication of OctaAPOSS/NO-PCL(1:10) and DETA/NO-PVAc (1:10) e-spun fibers can not only be fabricated as flats sheet but also in the form of hollow tubes. Furthermore, the ability of NO to inhibit thrombogenecity, promotion of endothelialization and inhibition of smooth muscle cell migration, motivated the fabrication of electrospun small diameter vascular graft conduits with NO-releasing properties. A vascular graft with NO-releasing capabilities, exhibiting these desirable characteristics, would better mimic native blood vessels. Obtaining sustained and controlled NO release for 220 d from our elastomeric composite makes this novel material a highly appropriate candidate for application towards blood-vessel replacement and other therapeutic applications.

Fabrication of a hollow tube was achieved by collecting the fibers rather on a smaller mandrel (≦7 mm) instead of a 50 mm mandrel. The idea behind the hollow NO-releasing tube is to apply it as a synthetic vascular graft conduit for treatment of vascular diseases. FIG. (7) shows a picture of a hollow tube conduit according to the present invention prepared by the electrospinning method aforementioned.

Thickness of the tube inherently affects the modulus of the composite, thus the volume of solution electrospun was used to control the thickness (see FIG. 8). Table 1 below shows the relationship between tube thickness and thermal properties

TABLE 1

| Tube Thickness (mm) | E-spinning time (h) | Modulus (MPa) | $T_m$ (° C.) | $\Delta H$ (J/g) | Ratio $\Delta H_{tube}/\Delta H_{PCL}$ |
|---|---|---|---|---|---|
| 0.42 | 0.67 | 1.1 | 54.3 | 7.24 | 0.16 |
| 0.30 | 1.5 | 2.5 | 54.0 | 2.84 | 0.07 |
| 0.18 | 3 | 3.7 | 54.2 | 1.74 | 0.04 |

Electrospinning a volume of 1 ml of PCL-POSS/NO solution yields a tube of 300 microns thickness after infiltration of PDMS, with a modulus generally around ≦7.6 MPa, which not only exhibits adequate mechanical properties but also exhibits NO-releasing functionality. This particular vascular graft conduit provides an advantage over current commercially available vascular grafts. The NO-release concentration can be tailored by varying the electrospinning volume and quantity of the NO-donor respectively. In addition, the shape-memory property of PVAc and PCL elastomeric fibers composites enable shape fixing prior to insertion, which is particularly beneficial for irregular bends present within blood vessels, as it helps to inhibit kinking or blockage of the graft during and after insertion, as seen in FIG. 9.

Table 2 below includes a list of compounds which may be used for the fibers, the matrix and the NO donor, in any combination.

| Matrix | Fiber | NO Donor |
|---|---|---|
| Elastomeric | poly(vinyl acetate) | Sodium (Z)-1-(N,N-Diethylamino)diazen-1-ium-1,2-diolate] (DEA-NO) |
| poly(dimethyl siloxane), crosslinked | poly(ε-caprolactone) | 1-[N-(2-Aminoethyl)-N-(2-ammonioethyl)amino]diazen-1-ium-1,2-diolate (DETA-NO) |
| polyurethane-based thermoplastic elastomers | polystyrene | Disodium1[(Carboxylato)pyrrolidin-1-yl]diazen-1-ium-1,2-diolate] (PROLI-NO) |
| crosslinked polyurethane elastomers | Nylon-6 | 1-{N-[3-Aminopropyl]-N-[(3-aminopropylammoniobutyl)]}diazen-1-ium-1,2-diolate (SPER-NO) |

-continued

| Matrix | Fiber | NO Donor |
|---|---|---|
| vulcanized styrene-butadiene random copolymer | Nylon-12 | Cation Stabilized Diazeniumdiolate POSS-(NHNONO-K$^+$)$_8$ (OctaAPOSS/NO) |
| crosslinked poly(isobutylene) | Polyamides (various) | POSS-poly(ethylene imine)/NO POSS-(PEI)$_8$-(NO)$_{16}$ |
| crosslinked cis-polyisoprene (vulcanized natural rubber) | poly(methyl methacrylate) | |
| crosslinked cis-polybutadiene | poly(styrene) | |
| Chloroprene rubber | poly(alkyl methacrylate) copolymers | |
| Styrene-butadiene-styrene triblock copolymer thermoplastic elastomers | Poly(ethylene terephthalate) | |
| General: diblock, tri-block, or multibock copolymers with at least one block that is crystalline or glassy and one block that is elastomeric | Polycarbonate | |
| Crosslinked poly(alkyl acrylate) | polyurethane-based thermoplastic elastomers | |
| plasticized PVC | Styrene-butadiene-styrene triblock copolymer thermoplastic elastomers | |
| Polyamide-polyether multiblock copolymer thermoplastic elastomers, such as PEBAX ™ | General: diblock, tri-block, or multibock copolymers with at least one block that is crystalline or glassy and one block that is elastomeric | |
| Glassy or Semicrystalline Crosslinked poly(ethylene oxide) | | |
| Crosslinked poly(ε-caprolactone) | | |
| poly(methyl methacrylate) | | |
| poly(styrene) | | |
| poly(alkyl methacrylate) copolymers | | |
| Poly(ethylene terephthalate) | | |
| Polyamides (various) | | |
| Nylon-6 | | |
| Nylon-12 | | |
| Polycarbonate | | |

The present invention can be applied on surfaces of blood contacting medical devices such as catheters, stents, or vascular grafts, with the purpose of releasing nitric oxide within a controlled rate and for a sustained period of time—greater than one day, preferably greater than one week. During the application of blood contacting medical devices, there is a potential that damage can be induced on the fragile endothelium lining. As a result, the body tries to correct this problem by enabling smooth muscle cell proliferation, and this oftentimes causes intimal hyperplasia which leads to restenosis. Nitric oxide not only prevents platelet aggregation, it also inhibits the proliferation of smooth muscle cell while it enhances the proliferation of endothelium cells. Therefore, nitric oxide releasing compounds, such as our novel NO-modified OctaAmmoniumPOSS, will impart a number of beneficial biological functions. The same invention can be applied for a sustained antimicrobial effect so important for the prevention of nosocomial (hospital-acquired) infections, but also of value for odor prevention in footware and clothing.

Commercial potential exists for the anticipated vasodilation properties of the same invention. For example, the release media could be utilized for improved circulation and pain relief for patients suffering from diabetes or sickle cell disease. Also, the same release media could be used for enhanced and extended penile erection in the form of condoms or similar skin-contacting devices. It is known that the erection of the penis during sexual excitation is mediated by NO released from nerve endings close to the blood vessels in the penis. Thus, the invented NO-release media may serve as a release media for the treatment of erectile dysfunction. This would serve as an alternative to ingested drugs, sildefanil (Viagra™), vardenafil (Levitra™), and tadalafil (Clalis™) that function indirectly by inhibiting an enzyme that breaks down cyclic GMP, a messenger protein that signals vasodilation.

Finally, commercial potential exists for the media in enhancing the process of in-vitro fertilization of human embryos. It is know that the acrosome at the tip of the sperm head activates NO synthase when it enters the egg. The resulting release of NO in the egg appears to be important for triggering the next steps in the process, in particular blocking the entry of additional sperm and possibly orienting the pronuclei for fusion. The literature in this area is restricted to non-human fertilization studies; thus, this is highly speculative. However, it is possible that in-vitro fertilization upon substrates consisting of the present invention would be more productive than the same process upon conventional Petri dishes.

What is claimed is:

1. A system for releasing nitric oxide, comprising:
an electrospun fiber mat having a plurality of fibers and spaces formed between the fibers, wherein said fiber mat includes at least one nitric oxide modified fiber; and
an elastomeric matrix comprising an elastomeric composite infiltrated into the spaces formed between the fibers of said fiber mat to encapsulate said at least one nitric oxide modified fiber.

2. The system of claim 1, wherein said at least one at least one nitric oxide modified fiber comprises a diazeniumdiolate modified polymer.

3. The system of claim 2, wherein said diazeniumdiolate modified polymer is selected from the group consisting of an NO-modified OctaAmmoniumPOSS, a DETA/NO entrapped in electrospun linear poly(ethyleneimine) (LPEI), a poly(vinylpyrrolidone) (PVP), a poly(caprolactone) (PCL), a poly(vinyl acetate) (PVAc) and a PEI-POSS hybrid polymer.

4. The system of claim 3, wherein said at least one nitric oxide modified fiber has an average diameter of between about 100 nanometers and 500 nanometers.

5. The system of claim 1, wherein said elastomeric matrix comprises a crosslinked polydimethylsiloxane.

6. The system of claim 1, wherein said elastomeric matrix comprises a shape memory polymer.

7. A method of forming a nitric oxide releasing compound, comprising the steps of:
modifying a polymer to include a nitric oxide donor;
electrospinning said polymer to form a fiber mat having a plurality of fibers and spaces formed between the fibers; and
impregnating said fiber mat with an elastomeric matrix comprising an elastomeric composite so that the elastomeric matrix infiltrates into the spaces formed between the fibers of said fiber mat and encapsulates the fibers.

8. The method of claim 7, wherein the step of modifying a polymer to include a nitric oxide donor comprises reacting said polymer with nitric oxide under a predetermined pressure in an anoxic environment, under vacuum, for a predetermined period of time.

9. The method of claim 8, wherein said at least one at least one nitric oxide modified polymer comprises a diazeniumdiolate modified polymer.

10. The method of claim 9, wherein said diazeniumdiolate modified polymer is selected from the group consisting of an NO-modified OctaAmmoniumPOSS, a DETA/NO entrapped in electrospun linear poly(ethyleneimine) (LPEI), a poly(vinylpyrrolidone) (PVP), a poly(caprolactone) (PCL), a poly(vinyl acetate) (PVAc) and a PEI-POSS hybrid polymer.

11. The method of claim 7, wherein the step of electrospinning said polymer to form a fiber mat comprises electrospinning said polymer to form polymeric fibers having an average diameter of between about 100 nanometers and 500 nanometers.

12. The method of claim 7, wherein the step of impregnating said fiber mat with an elastomeric matrix comprises infiltrating said fiber mat with an elastomer and cross-linking said elastomer by curing said elastomer.

13. The method of claim 10, wherein said elastomeric matrix comprises a crosslinked polydimethylsiloxane.

14. The system of claim 10, wherein said elastomeric matrix comprises a shape memory polymer.

* * * * *